US00PP21710P3

(12) United States Plant Patent
Barritt

(10) Patent No.: US PP21,710 P3
(45) Date of Patent: Feb. 15, 2011

(54) APPLE TREE NAMED 'WA 2'

(50) Latin Name: *Malus domestica*
Varietal Denomination: WA 2

(75) Inventor: Bruce H. Barritt, Okanagan Centre (CA)

(73) Assignee: Washington State University Foundation, Pullman, WA (US)

( * ) Notice: Subject to any disclaimer, the term of this patent is extended or adjusted under 35 U.S.C. 154(b) by 0 days.

(21) Appl. No.: 12/383,556

(22) Filed: Mar. 24, 2009

(65) Prior Publication Data

US 2010/0251440 P1 Sep. 30, 2010

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

PP4,121 P 10/1977 Ten Hove
PP7,880 P 6/1992 Cripps

OTHER PUBLICATIONS

The Apr. 24, 2007 Test Agreement for Testing Apple Selections and Cultivars Developed by Washington State University, between Washington State University and Pepin Heights Orchards, Inc., 5 pages.
The Apr. 24/25, 2007 Test Agreement for Testing Apple Selections and Cultivars Developed by Washington State University, between Washington State University and Lynoaken Farms, Inc., 5 pages.
The Apr. 24/25, 2007 Test Agreement for Testing Apple Selections and Cultivars Developed by Washington State University, between Washington State University and Wittenbach Orchards, Inc., 5 pages.
The Apr. 27, 2007 Test Agreement for Testing Apple Selections and Cultivars Developed at Washington State University, between Washington State University and Yakima Valley Orchards/Allan Bros. and Allan Bros., 8 pages.
The Apr. 27, 2007 Test Agreement for Testing Apple Selections and Cultivars Developed at Washington State University, between Washington State University and Crane & Crane, Inc., 8 pages.
The Apr. 27, 2007 Test Agreement for Testing Apple Selections and Cultivars Developed at Washington State University, between Washington State University and Columbia Fruit Packers, Inc., 8 pages.
The Apr. 27, 2007 Test Agreement for Testing Apple Selections and Cultivars Developed at Washington State University, between Washington State University and Stemilt Growers, Inc. and Highway 28, LLC, 8 pages.
The Apr. 28, 2008 Test Agreement for Testing Apple Selections and Cultivars Developed at Washington State University, between Washington State University and Crane & Crane, Inc., 7 pages.
The Apr. 28, 2008 Test Agreement for Testing Apple Selections and Cultivars Developed at Washington State University, between Washington State University and Stemilt Growers, Inc. and Highway 28, LLC, 8 pages.
The Jun. 7, 2007 Agreement to Propagate and Distribute for Test Purposes Only Washington State University Plant Selections and Cultivars, between Washington State University and Willow Drive Nursery, 7 pages.

*Primary Examiner*—Kent L Bell
(74) *Attorney, Agent, or Firm*—Morrison & Foerster LLP

(57) ABSTRACT

A new and distinctive variety of an *Malus domestica* 'apple' tree, named 'WA 2', that is distinguished by its attractive blush, outstanding texture being firm, crisp and juicy, and the presence of the homozygous genes for ethylene production ACS1-2/2 and ACO1-2/2 which contribute to maintaining the fruit quality over long periods of storage.

4 Drawing Sheets

Latin name of the genus and species of the claimed plant

Botanical/commercial classification: *Malus domestica*/ apple tree

Varietals denomination: 'WA 2' seedling designation T19-17-3-9427

The invention refers to a new plant variety of apple tree (*Malus domestica*) named 'WA 2'. This new variety is distinguished by the distinctive blush of its fruit, with the texture being firm, crisp and juicy even after 60 days of regular cold storage due to the presence of the homozygous genes for ethylene production, ACS1-2/2 and ACO1-2/2.

BACKGROUND OF THE INVENTION

'WA 2' (seedling designation T19-17-3-9427) originated from a seed collected in 1994 from fruit of the 'Splendour' cultivar. The male parent is 'Gala'. The germinated seedling was grown in a greenhouse at Wenatchee, Wash. during the summer of 1995. In September 1995, a bud from the seedling was budded to M9 rootstock and the resulting tree was planted in the evaluation orchard at Wenatchee, Wash. in the spring of 1997. Fruit from the originally budded 'WA 2' tree were evaluated in 2000 and 2001. Second generation trees were produced by chip-budding to M9 rootstock Fall of 2002 and the resulting trees planted at three locations in Washington State in 2004 near Chelan, Wash., Chelan County; near Wenatchee, Wash., Douglas County; and near Basin City, Wash., Franklin County. Fruit from the second generation trees at all three orchard locations were compared to that of the originally budded tree in 2005, 2006, 2007, and 2008, and found to be essentially similar to that of the originally budded tree.

SUMMARY OF THE INVENTION

'WA 2' is an attractive apple that is distinct in appearance from that of other commercially grown apples and has outstanding texture, being very firm, crisp and juicy, both fresh and after 60 days of regular cold storage. Firmness is comparable to the commercial varieties of 'Cripps Pink' and 'Braeburn' and is firmer than the commercial varieties 'Gala' and 'Fuji' (Table 1, second column). Fruit of 'WA 2' is sweet with percent soluble solids greater than for 'Gala' and 'Braeburn' and is comparable to 'Fuji' and 'Cripps Pink' (Table 1, third column). Fruit acidity level of 'WA 2' is intermediate between low acidity cultivars 'Gala' and 'Fuji' and high acidity cultivars 'Braeburn' and 'Cripps Pink' (Table 1, fourth column). Overall flavor is well balanced between sugar and acid. When compared to its maternal parent 'Splendour', 'WA 2' has higher levels of acidity and sweetness, and is firmer. While similar in size to 'Gala', 'WA 2' is larger than 'Splendour' and has a brighter, more orange/red appearance than either parent. The 'WA 2' tree also differs from 'Gala' in that it reaches harvest maturity around 5 weeks later than 'Gala'. 'WA 2', like its maternal parent, is homozygous for the ethylene production gene Md-ACS1. In addition it is homozygous for a second ethylene production gene Md-ACO1. The ACS and ACO genotypes were determined by fragment analysis of the results of polymerase chain reactions using the primers published by Harada et al. (2000) and Costa et al. (2005).

DETAILED BOTANICAL DESCRIPTION

Figure 1:
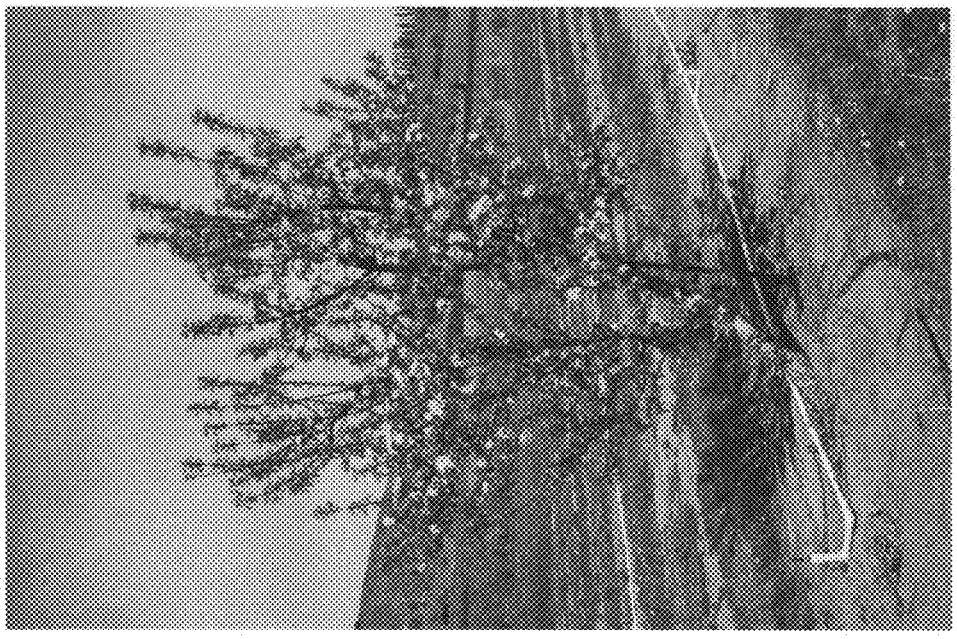
FIG. 1. The eight year old originally budded tree of 'WA 2' on M9 rootstock near full bloom.

The following detailed description is from the originally budded 'WA 2' tree grown at Wenatchee, Wash. The 'WA 2' tree was 14 years old when measurements were taken. All color references are from the RHS colour chart by The Royal Horticultural Society.

Tree

Type: considered spur type with development mostly on 2 yr. old wood, some on current seasons growth; spur length ranges from 1 to 8 cm

*Vigor.*—considered moderate, with seasonal growth ranging from 46 to 91 cm, and an average of 75 cm.

*Overall Shape.*—upright and spreading.

*Height.*—14 feet.

*Width.*—7 feet.

*Hardiness.*—considered hardy for the regions grown in; USDA hardiness zone is 7.

*Productivity.*—considered very productive, exhibits alternate bearing tendencies if over-cropped the previous season.

Trunk:

*Size.*—diameter at a height of 45 cm is 11.4 cm.

*Bark texture.*—smooth.

*Bark color.*—from the greyed-orange group (177A).

*Lenticels.*—numerous, with an average of 2 lenticels per 4 $cm^2$, and horizontal to the plane, size averages 9.9 mm×1.8 mm.

*Lenticels color.*—from the brown group (200C).

Branches:

*First year branches.*—considered moderate in number with light spur development; spreading habit with moderate crotch angles of 0° to 35°; growth ranges from 46 to 91 cm with an average of 75 cm; and diameter ranges from 0.8 to 1.4 cm with an average of 1.1 cm. Color: from the greyed-purple group (187A). Lenticels: round to slightly elongated and oriented parallel to growth with color from the white group (N155D); size average is 0.5 mm×1 mm; density is at 11 per running cm. Branch pubescence: present, moderate, with color from the white group (155D). Internodes: spacing averages 4.2 cm.

*Scaffold branches.*—moderate in number; spreading habit with crotch angles of 30°-80°; diameter ranges from 7.6 to 11.4 cm with an average of 9.1 cm. Color: from the grey-brown group (N199D). Lenticels: numerous, with an average of 6 lenticels per 4 $cm^2$, and horizontal to plane, rough; averages 10.2 mm×2.1 mm in size.

*Lenticels color.*—from the white group (N155C).

Leaves:

*Shape.*—considered oval.

*Texture.*—considered leathery.

*Sheen.*—upper surface is glossy.

*Pubescence.*—lower surface is covered with fine pubescence.

*Length.*—ranges from 7.2 to 10.5 cm; average length is 9.2 cm.

*Width.*—ranges from 4.6 to 7.3 cm; average length is 6.0 cm.

*Margin.*—considered double serrate.

*Tip.*—considered cuspidate.

*Base.*—considered obtuse.

*Stipules.*—present on most leaves; average number per leaf is 0.8 with a range of 0 to 2 per leaf; average length is 6.3 mm; width ranges from 0.8 to 1.0 mm; both upper and lower stipule surfaces have color from the green group (142D).

*Leaf color.*—upper surface from the yellow-green group (147A); lower surface from the yellow-green group (147B).

*Petiole.*—lengths range from 2.2 to 3.9 cm, average is 3.3 cm; average diameter is 1.7 mm; color is from the green group (142D) with high lights from the greyed-purple group (186A).

*Bud.*—shape is conic; length ranges from 0.7 to 0.85 cm with an average of 0.8 cm; diameter at base ranges from 0.32 to 0.51 cm with an average of 0.43 cm; tip is considered more rounded than obtuse; base is considered truncate; and color is from the brown group (200C).

*Flowers.*—Full bloom date May 5, 2008 at Wenatchee, Wash.; number of blossoms per bud ranges from 4 to 6-mostly 5-with an average of 4.6 blossoms per bud.

*Depth.*—ranges from 17.3 to 23.1 mm with an average of 21.1 mm for flower petals folded back up; and ranges from 2 to 4 mm with an average of 3 mm for flower where the petals attach at their base to the base of the ovary.

*Aroma.*—mildly sweet aromatic typical of apple blossoms.

*Size.*—individual flowers considered medium in size averaging 50.2 mm across.

*Petal.*—width averages 17.9 mm; length averages 21.1 mm; number of petals is five per bloom, with no range noted; shape is considered obovate; shape of tip is rounded; shape of base is considered rounded; margin is smooth; and the surface is considered smooth.

*Color.*—from the white group (N155B) for both upper and lower surface of petal; upper surface of the petal is highlighted from the greyed-purple group (186D), whereas the lower surface is highlighted from the red-purple group (63B); and petal vein color for both the upper and lower surfaces is from the greyed-purple group (186B).

*Stamen.*—range of 20-22 mm length with an average length of 20.7 mm Filament: color is from the green-yellow group (1D) Anthers: color at maturity from the yellow group 4C; average length is 2.1 mm.

*Pistil.*—one imperfectly syncarpic pistil per flower; average length is 7.9 mm Styles: 4 to 6 in number generally 5, fused at base and pubescent at union; average length is 3.2 mm; color is from the yellow-green group (154C) Stigma: club shaped; color is from the yellow-green group (154B).

*Sepals.*—five per bloom and occasionally curled back towards the peduncle; average length is 7.2 mm and average width is 4.2 mm; shape is considered deltoid with the tip being considered acuminate and the base is considered truncated; margins are smooth; surface is smooth; colorless pubescence is present on both upper and lower surfaces; sepal color for both upper and lower surface is from the green group (138B) with tips highlighted from the greyed-red group (178B).

*Pollen.*—produced and quantity is moderate, which is typical for *Malus* sp; color is from the yellow group (4C).

*Fruit.*—observations and testing from originally budded tree fruit part from yield data.

*Size.*—considered medium averaging 7.7 cm in equatorial diameter and 7.0 cm in axis diameter.

*Amount.*—Typical yield from 5 year old second generation trees averaged 126 per tree in a season, with an average fruit weight of 181 grams (yield data from the original mother tree is not representative due to the seedling orchard growing system that was used).

*Form.*—considered round-conical.

*Stem.*—medium reaching above stem bowl and averaging 2.3 cm in length; medium stout averaging 3.3 mm in diameter at midpoint; exhibits pronounced clubbed end; and color is from the green group (142D).

*Stem Cavity.*—average width is 2.9 cm; average depth is 1.7 cm.

*Cavity shape.*—acuminate.

*Lipped.*—no.

*Basin Cavity.*—average width is 31.2 mm; average depth is 17.6 mm; some light ribbing.

*Calyx.*—eye is generally erect.

*Skin.*—smooth with bloom present.

*Appearance.*—blush over 75-95% of surface.

*Lenticels.*—numerous, distinct, ranging from 6-15 per square cm.

*Lenticels size.*—round and ranging from 0.3-0.7 mm in diameter; color from the white group (157D).

*Skin Color.*—blush color is from the red group (47A); undercolor is from the yellow group (4C).

*Core.*—core line attachment is medium; length ranges from 22.7 to 31.6 mm with an average of 27.9 mm; width ranges from 34.2 to 39.7 mm with an average of 36.7 mm.

*Core position.*—is distant.

*Cell (locule or carpel).*—5 per fruit; not tufted; shape is obovate; length ranges from 12.0 to 17.3 mm with an average of 14.8 mm; and width ranges from 10.1 to 12.9 mm with an average of 11.2 mm.

*Tube.*—funnel shaped.

*Sepals.*—contain white downy hairs.

*Stamen position.*—medium relative to stamens situated approximately in the middle of the tube (the cavity just beneath the eye).

*Cell attachment to axis.*—axile and closed, meaning cells are symmetrical and each cell is closed.

*Seed.*—Number: 1-4 per cell with an average of 3 Shape: acute; size averages 4.5 mm in diameter×8.1 mm in length Color: from the brown group (200D).

*Flesh.*—firm, crisp, melting texture, considered mildly acidic with excellent sugar balance; color from the yellow-white group (158D).

*Eating quality.*—Considered best, being firm, crisp, and mildly acidic with excellent sugar balance.

*Aroma.*—mild, apple like.

*Date of harvest maturity.*—Late September/early October. Usually around 5 weeks after 'Gala' and at a similar time to 'Splendour'.

*Maturity indices.*—Starch: Cornel chart is 3.6 Pressure: in Newtons is 77.0 Soluble Solids: in ° Brix is 13.9 Titratable Acid: as mg/l malic acid is 0.43.

*Genotype.*—'WA 2' is homozygous for the ethylene production genes Md-ACS1 and Md-ACO1.

*Keeping quality.*—excellent, exceeding 90 days in common storage with little to no loss in firmness and acidity.

Pollination: any diploid apple of the same bloom season.

Use: primarily for fresh eating.

Disease and Insect Resistance: considered susceptible to all apple insects and has known susceptibility to apple powdery mildew; susceptibility to other apple diseases is unknown.

Table 1 represents fruit indices of the 'WA 2', 'WA 2' second generation, 'Gala', 'Braeburn', 'Cripps Pink' and 'Fuji' varieties at harvest maturity and following 60 days in common storage. The differences between fruit from the 'WA 2' originally budded tree and from the 'WA 2' second generation trees are as expected from an apple cultivar grown in different environments.

TABLE 1

Fruit indices at harvest maturity and following 60 days in common storage

| | Firmness Newtons | | Sugars % Soluble solids | | Acidity mg/l malic acid | | |
|---|---|---|---|---|---|---|---|
| Cultivar | Fresh | Storage | Fresh | Storage | Fresh | Storage | Year |
| 'WA 2' | 77 | 70 | 13.9 | 14.3 | 0.43 | 0.35 | 2008 |
| 'WA 2' $2^{nd}$ gen. | 81 | 76 | 13.9 | 14.0 | 0.51 | 0.40 | 2008 |
| 'Gala' | 72 | 73 | 13.3 | 14.1 | 0.58 | 0.34 | 2008 |
| 'Braeburn' | 86 | 82 | 14.5 | 15.4 | 0.87 | 0.51 | 2008 |
| 'Cripps Pink' | 84 | 82 | 15.6 | 16.0 | 0.94 | 0.66 | 2008 |
| 'Fuji' | 72 | 64 | 14.5 | 15.7 | 0.56 | 0.46 | 2008 |

Figure 2:
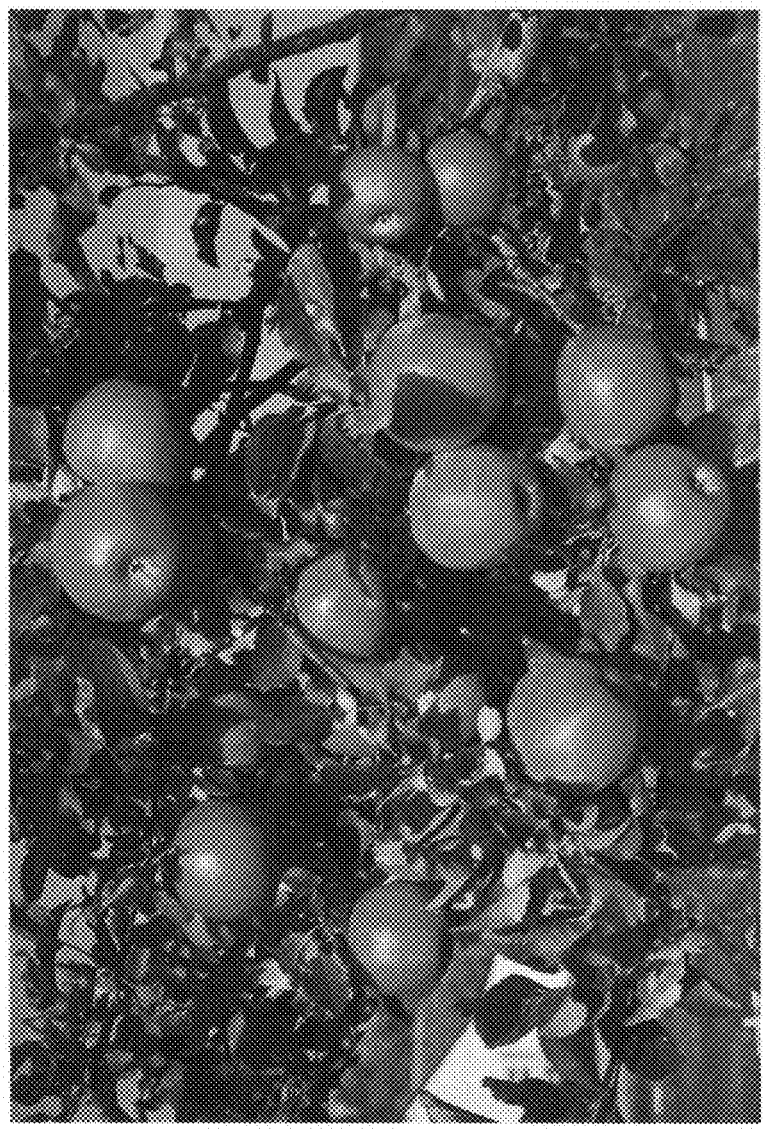
FIG. 2. 'WA 2' originally budded tree fruit at harvest maturity.
Figure 3:
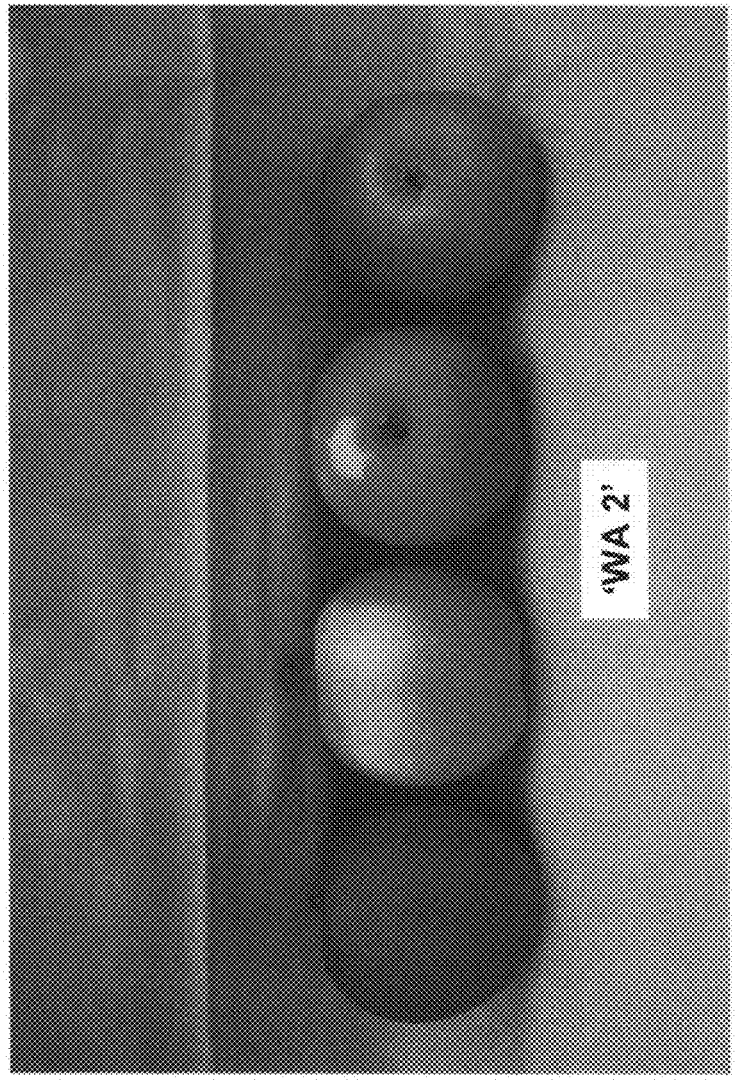
FIG. 3. View of 'WA 2' fruit showing exposed and backsides, and stem and calyx ends.
Figure 4:
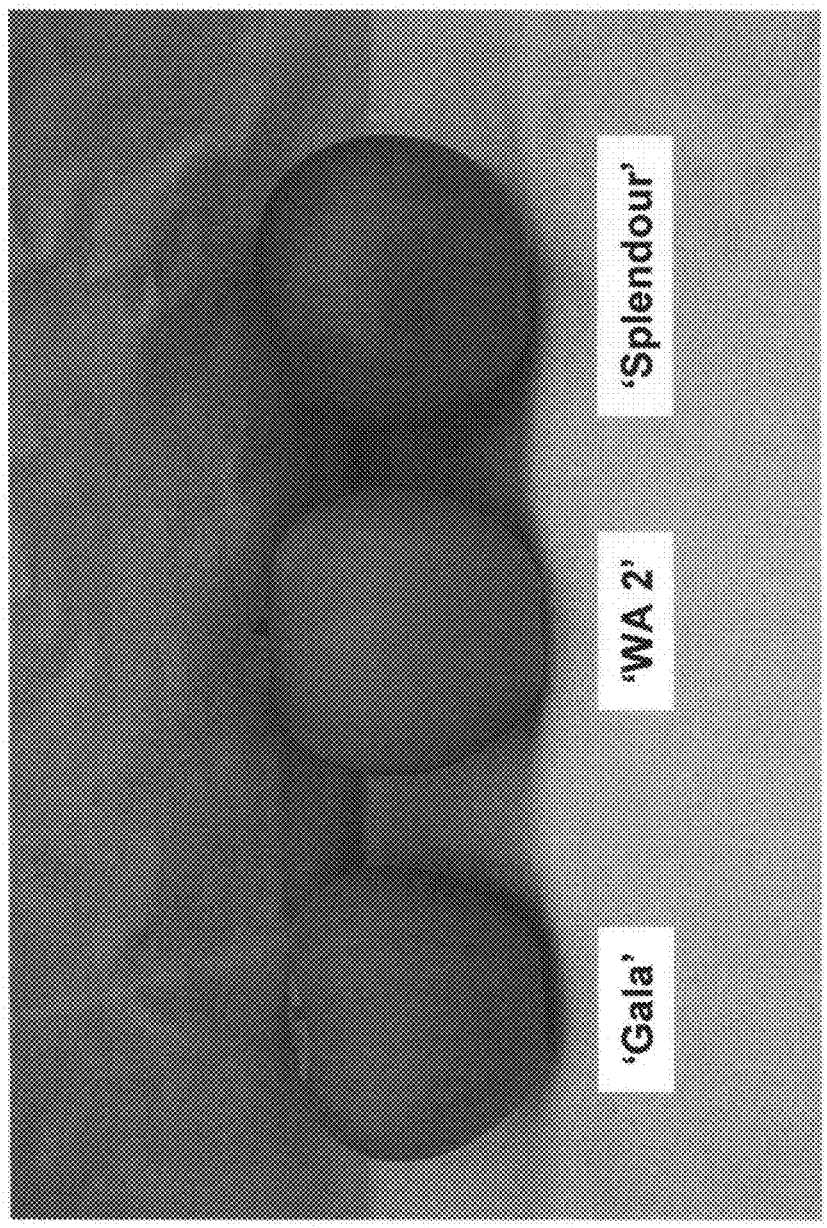
FIG. 4. View of typical 'Tenroy Gala', 'WA 2' and 'Splendour' apples at harvest maturity.

The attached figures show the 'WA 2' tree and various aspects of its fruit. FIG. 1 is a photo of the eight year old originally budded tree of 'WA 2'. FIG. 2 is a close up of the apples at harvest maturity on the originally budded tree. FIG. 3 shows representative views of the exposed and backsides of the 'WA 2' fruit, in addition to the stem and calyx ends of the fruit. FIG. 4 shows the 'WA 2' fruit as compared to the fruit of its two parental varieties at harvest maturity. A typical 'Tenroy Gala' apple, suspected of being the male parent cultivar, and a typical 'Splendour' apple, are show next to a 'WA 2' apple.

What is claimed:

1. A new and distinct apple tree variety named 'WA 2', as herein shown and described.

* * * * *